United States Patent [19]

Jagdmann, Jr. et al.

[11] Patent Number: 5,070,095
[45] Date of Patent: Dec. 3, 1991

[54] SUBSTITUTED 4-(AMIDINO)BENZAMIDES OF 1-AZABICYCLO[2.2.2]OCTAN-3- AND -4-AMINE AS GASTRIC PROKINETIC, ANTIEMETIC, AND ANXIOLYTIC AGENTS

[75] Inventors: Gunnar E. Jagdmann, Jr.; Harry R. Munson, Jr., both of Durham, N.C.

[73] Assignee: A. H. Robins Company, Incorporated, Richmond, Va.

[21] Appl. No.: 626,437

[22] Filed: Dec. 12, 1990

[51] Int. Cl.$^5$ .................. A61K 31/435; C07D 221/02
[52] U.S. Cl. ..................................... 514/305; 546/133
[58] Field of Search .......................... 546/133; 514/305

[56] References Cited

U.S. PATENT DOCUMENTS 4,593,034  6/1986  Munson et al. ...................... 514/305
4,657,911  4/1987  Imbert et al. ........................ 514/272

OTHER PUBLICATIONS

Chem. Abs. 100, 174466e (Abstract of Spanish Patent ES 516729A1).

J. Med. Chem. 31, 1548–1558 (1988), Monkovic et al.

Primary Examiner—Richard L. Raymond
Attorney, Agent, or Firm—George Tarnowski

[57] ABSTRACT

Novel 1-(azabicyclo[2.2.2]oct-3- or -4-yl)benzamides substituted on the benzene ring with the basic substituted aminomethyleneamino group have been found to be useful in treating emesis, including emesis due to chemical and radiation anticancer therapy, anxiety, and impaired gastric emptying. These compounds are represented by Formula I below.

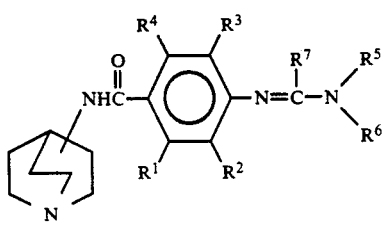

Formula I

10 Claims, No Drawings

SUBSTITUTED 4-(AMIDINO)BENZAMIDES OF 1-AZABICYCLO[2.2.2]OCTAN-3- AND -4-AMINE AS GASTRIC PROKINETIC, ANTIEMETIC, AND ANXIOLYTIC AGENTS

BACKGROUND OF THE INVENTION

1. Field of Invention

This invention relates to 4-amidinobenzamides of 1-azabicyclo[2.2.2]octane-3- and -4-amines (3- and 4-aminoquinuclidines) which have antiemetic, gastrokinetic, and anxiolytic properties. These compounds differ from other quinuclidine benzamides in that the phenyl ring is substituted with a basic amidino group.

2. Information Disclosure Statement

Several patents disclose benzamides of 1-azabicyclo[2.2.2]octan-3-amine and 1-azabicyclo[2.2.2]octan-4-amines having amine substituents on the benzene ring portion of the molecule. However, the amine substituents claimed are limited to amino, monoalkyl or dialkylamino or alkylcarbonylamino.

1-Azabicyclo[2.2.2]octan-3-amine benzamides of the formula:

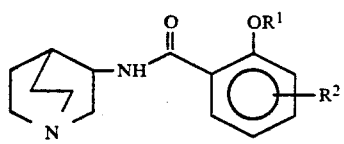

where $R^1$ is loweralkyl and $R^2$ is amino, methylamino, or dimethylamino are disclosed in U.S. Pat. Nos. 4,593,034 and 4,722,834. Other benzamides of the formula:

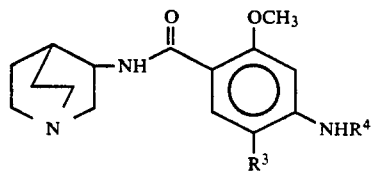

where $R^3$ is halogen and $R^4$ is H or alkylcarbonyl are disclosed in U.S. Pat. No. 4,657,911. Similar benzamides of 1-azabicyclo[2.2.2]octan-4-amine are disclosed in the European patent application 202,062A which have the formula:

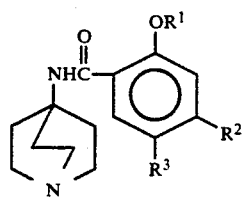

where $R^1$ is $C_1-C_6$ alkyl, $R^3$ is halogen and $R^2$ is amino, $C_1-C_7$ acylamino, or methyl.

A Spanish patent, ES 516,729A, describes antiemetic compounds of the formula:

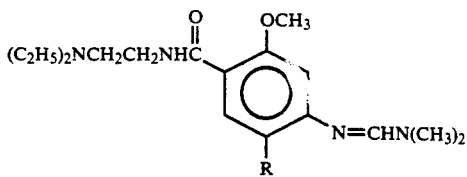

where R is bromine or chlorine. The 5-chloro substituted compound is described as a chemical intermediate in *J. Med. Chem.* 1988, 31, 1548-1558, where the dimethylaminomethylene group functions as a protecting group in a synthetic scheme. The N-(1-azabicyclo[2.2.2]octan-3- or -4-yl)-4-[[(substitutedamino)methylene]amino] benzamides of this invention are novel.

SUMMARY OF THE INVENTION

The compounds of this invention are useful in mammals, including humans, as gastric promotility agents, in treating anxiety and in treating emesis including emesis caused by chemical and radiation anticancer therapy. These compounds are represented by Formula I:

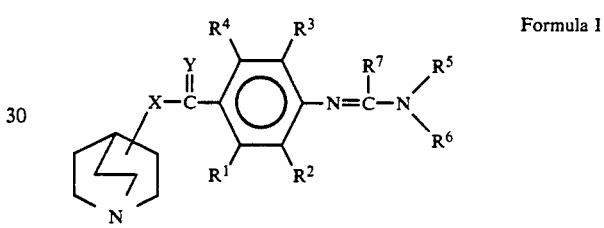

Formula 1 wherein X=NH attached to 3 or 4 position of 1-azabicyclo[2.2.2]octane, Y is O or S, $R^1$, $R^2$, $R^3$ and $R^4$ are independently selected from the group consisting of H, halogen, $C_1-C_4$ alkyl, $C_2-C_4$ alkenyl, $C_1-C_4$ alkoxy, and OH; $R^5$ and $R^6$ are independently selected from the group consisting of H, $C_1-C_4$ alkyl, cycloalkyl, or $R^5$ and $R^6$ together with the interposed nitrogen forms a 5 or 6 membered heteroalicyclic ring; and $R^7$ is H or methyl.

This invention also encompasses the stereoisomers where possible and the pharmaceutically acceptable salts which include the acid addition salts, hydrates, solvates, and N-oxides. Acid addition salts include the salts formed from inorganic or organic acids such as hydrochloric acid, hydrobromic acid, sulfuric acid, phosphoric acid, fumaric acid, succinic acid, maleic acid, hexamic acid, citric acid, methanesulfonic acid, oxalic acid and the like.

It is therefore an object of this invention to provide novel substituted aminomethyleneamino substituted benzamides of 1-azabicyclo[2.2.2]oct-3- or 4-yl amines. Another object is to provide methods of treating warm-blooded animals, including humans, to alleviate emesis, including emesis due to the chemotherapy with drugs such as cis-platin, doxorubicin, dactinomycin, dacarbazine, or mechlorethamine hydrochloride or radiation therapy used in cancer treatment, to facilitate gastric emptying, and to alleviate anxiety symptoms.

It is another object to provide pharmaceutical compositions to be used in the foregoing methods of treatment.

DETAILED DESCRIPTION OF THE INVENTION

The object compounds of this invention are prepared by reacting a benzamide containing an amino group with an appropriately substituted formamide or acetamide dialkylacetal as shown in the following reaction scheme:

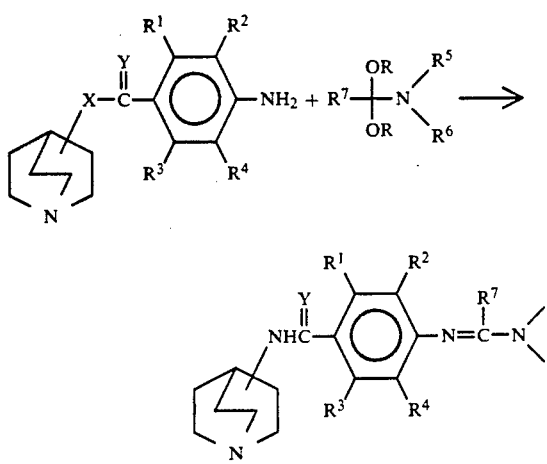

The reaction is carried out by heating the reactants together in a solvent such as toluene or dimethylformamide. The products are isolated and purified by procedures known to those skilled in the art such as chromatography, distillation, crystallization, salt formation, extraction, and the like.

Stereoisomers may be obtained from products derived from 1-azabicyclo[2.2.2]octan-3-amine. The benzamides may be prepared from the enantiomers of 1-azabicyclo[2.2.2]octan-3-amine or the enantiomeric benzamides obtained from the racemic amine can be separated by conventional methods known to those skilled in the art. Tertiary amine oxides are obtained by oxidizing the nitrogen of the 1-azabicyclo[2.2.2]octane ring system either before or after reaction with the acetamide or formamide acetals with a peroxide using standard reaction conditions well known to those skilled in the art. Likewise, thioamides can be prepared from the benzamides of this invention by reacting with sulfurizing reagents such as potassium sulfide and phosphorus pentasulfide either before or after the reaction with acetamide or formamide acetals. Antiemetic activity is measured by a modification of the method of Gylys et al., Res. Comm. Chem. Path. Pharm., 23, 61 (1979). Gastric emptying properties are determined by the procedure of Droppleman et al., J. Pharmacol. Methods, 4, 227 (1980). Anxiolytic properties are determined using the procedure described by Young and Johnson, Neurosci. Abs. 1988, 14, 207. Compounds of this invention bear resemblance to other benzamides of bicyclic amines which have selective serotonin inhibiting or modulating properties and thus may have potential in the treatment of migraine, psychosis, certain arrhythmias, and improvement of cognitive deficiency. The compound of Example 1 has a $pA_2$ value of 6.3 against serotonin-induced contraction in guinea-pig ileum.

The foregoing methods of preparation of Formula I compounds are broadly described and other methods of preparation as well as limitations of the procedures given will be apparent to those skilled in the art. Exact conditions may vary with the substrates, solvents, reagents, temperature and the like. It is believed that one skilled in the art will be able to carry out this invention without undue experimentation. The following examples are therefore to be construed as illustrative and not limiting to this disclosure in any way. The various reagents used are either commercially available or readily synthesized by literature procedures.

EXAMPLE 1

N-(1-Azabicyclo[2.2.2]oct-3-yl)-5-chloro-4-[[(dimethylamino)methylene]amino]-2-methoxybenzamide A solution of 4-amino-N-(1-azabicyclo[2.2.2]oct-3-yl)-5-chloro-2-methoxybenzamide (4.03 g, 13 mmol) in dimethylformamide dimethyl acetal (15 mL) and anhydrous dimethylformamide (5 mL) was heated to 100° C. for 4 hours, then concentrated in vacuo. The residue was dissolved in 6:1 tetrahydrofuran/methanol and filtered through a short column of alumina (eluted with 6:1 tetrahydrofuran/methanol). The filtrate was concentrated in vacuo to a purple residue, which was triturated from cold ether and recrystallized (2 crops) from acetonitrile to afford 2.88 g (61%) of fine colorless needles; mp 178.5°–179.5° C.

Analysis: Calculated for $C_{18}H_{25}ClN_4O_2$: C, 59.25; H, 6.91; N, 15.35. Found: C, 59.24; H, 7.02; N, 15.29.

EXAMPLE 2

N-(1-azabicyclo[2.2.2]oct-3-yl)-5-chloro-4-[[1-(dimethylamino)ethylene]amino]-2-methoxybenzamide Following the procedure of Example 1, the title compound is prepared from 4-amino-N-(1-azabicyclo[2.2.2]oct-3-yl)-5-chloro-2-methoxybenzamide and N,N-dimethylacetamide dimethylacetal.

EXAMPLE 3

N-(1-azabicyclo[2.2.2]oct-3-yl)-5-chloro-4-[[(1-pyrrolidinyl)methylene]amino]-2-methoxybenzamide Following the procedure of Example 1, the title compound is obtained from 4-amino-N-(1-azabicyclo[2.2.2]oct-3-yl)-5-chloro-2-methoxybenzamide and N-formylpyrrolidine dimethylacetal.

EXAMPLE 4

N-(1-azabicyclo[2.2.2]oct-4-yl)-5-chloro-4-[[(dimethylamino)methylene]amino]-2-methoxybenzamide Following the procedure of Example 1, the title compound is obtained from 4-amino-N-(1-azabicyclo[2.2.2]oct-4-yl)-5-chloro-2-methoxybenzamide and N,N-dimethylformamide dimethylacetal.

EXAMPLE 5

N-(1-azabicyclo[2.2.2]oct-3-yl)-5-chloro-4-[[(dimethylamino)methylene]amino]-2-hydroxybenzamide Following the procedure of Example 1, the title compound is prepared from 4-amino-N-(1-azabicyclo[2.2.2]oct-3-yl)-5-chloro-2-hydroxybenzamide and N,N-dimethylformamide dimethylacetal.

PHARMACOLOGY METHODS AND COMPOSITIONS

A. Effect of Invention Compounds on Cisplatin-Induced Emesis In Dogs

The procedure used to test compounds of the present invention for antiemetic properties is a modification of the method of Gylys et al., Res. Commun. Chem. Pathol. Pharm., 23, 61 (1979).

Adult, mongrel, unfasted dogs of both sexes are randomly assigned into treatment groups, with each treatment group consisting of four dogs. On the dosing day all dogs are given cisplatin, 3.0 mg/kg, intravenously. Sixty minutes later, the dogs in the control treatment group are given deionized water, 0.1 ml/kg intravenously. Dogs in the treatment group receive a test compound (1-10 mg/kg IV). All doses are administered as a solution by means of a syringe and needle, and each dog's emetic episodes are recorded for 5 hours after the administration of cisplatin. The compound of example 1 blocked cisplatin induced emesis by 100% at a dose of 1 mg/kg IV.

B. Effect of Invention Compounds on Gastric Emptying of a Test Meal in Fasted Rats The procedure used to test compounds of the present invention for gastric motility enhancing activity is that of Droppleman et al., J. Pharmacol. Methods, 4, 227 (1980).

Each animal is dosed intraperitoneally (9.0 mg/kg) with a test compound or control. After 30 minutes each animal is given 3 ml of a methylcellulose-based test meal formulation. Sixty minutes after administration of the test meal, each animal is sacrificed by cervical dislocation, and the stomach is removed and weighed. The stomach is cut open, rinsed and dried, and reweighed. This difference between the full and empty weights (amount of meal remaining in stomach) is subtracted from the weight of the original test meal to determine the meal amount emptied from the stomach during the test period. The compound of Example 1 increased gastric emptying by 39% over the control at a dose of 1 mg/kg IP.

C. Anxiolytic Test

Exploratory Light/Dark (mice)

This method has been described by Young and Johnson (1988) and is a modification of the procedure described by Costall and Naylor (1988). A two-compartment light-dark activity monitoring device (Digiscan Model RXYZCM16, Omnitech Electronics Inc., Columbus, Ohio) is used. A 90 W light source located 30 cm above the box provides light to the lit portion of the apparatus. Behavioral testing is conducted in a sound-attenuated, darkened room illuminated with red light (25 W red bulb) only.

Each animal (mouse) receives a dose or doses of either the test, reference, or control article. The animal is placed at the center of the illuminated area and the behavioral activity tallied over a 5 minute period by use of the Digiscan analyzer. Behavioral variables recorded included: the time spent in the lit and dark areas, the number of rearings in the lit and dark areas, the number of transitions between the lit and dark or dark and lit areas, the latency to make the first transition from the lit area to the dark area, rearing time in the lit and dark areas, locomotor time in the lit and dark areas, and resting time in the lit and dark areas. Appropriate statistical analyses for each measure are performed. Significant increases in one or more of the parameters associated with behavior of the animals in the lit area versus behavior in the dark area correspond to active nonsedating anxiolytic compounds. At a dose of 0.10 mg/kg IP of the Example 1 compound, 47% of the time was spent in the lit area and this value was found to be significant as compared to controls.

References: Young, R., Johnson, D.N. Soc. Neurosci. Abs. 1988, 14, 207. Costall, B.; Naylor, R. Brit. J. Pharmacol. 1988, 93, 985-993.

D. 5-HT Induced Contractions In Guinea Pig Ileum

The effect of invention compounds on the blockade of 5-HT induced contractions of the guinea pig ileum was determined by the method described by Richardson, Engel, Donatsch, and Stadler, Nature, 316, 126 (1985). The Example 1 compound had a $pA_2$ of 6.33 in this test.

PHARMACEUTICAL COMPOSITION

The pharmaceutical compositions used in the methods of this invention for administration to living animals are comprised of, as active ingredients, at least one of the compounds of Formula I according to this invention, in association with a pharmaceutical carrier or excipient. The compounds are thus presented in a therapeutic composition for oral, parenteral, or rectal administration. Thus for example, compositions for oral administration can take the form of elixirs, capsules, tablets or coated tablets containing carriers conveniently used in the pharmaceutical art. Suitable tableting excipients include lactose, potato and maize starches, talc, gelatin, stearic and silicic acids, magnesium stearate and polyvinyl pyrrolidones.

For parenteral administration, the carrier or excipient can be comprised of a sterile parenterally acceptable liquid, e.g., water or arachis oil contained in ampoules.

In compositions for rectal administration, the carrier can be comprised of a suppository base, e.g., cocoa butter or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable dosage will be consistent with the dosage form employed in single or multiple unit doses. The exact individual dosages, as well as daily dosages, will, of course, be determined according to standard medical principles under the direction of a physician or veterinarian.

The pharmacology tests suggest a contemplated oral dosage for treating emesis, delayed gastric emptying, and anxiety in humans will be in the range of 0.001 to 100 mg/kg of body weight which can be administered in divided doses taken 3-4 times daily. The amount of active compound administered need not be limited by these contemplations due to the uncertainty in transposing animal data to human treatment and the route of administration.

Other routes of administration such as subcutaneous, intramuscular, intravenous, etc. are possible with dosage forms being adapted to the situation as will be obvious to one skilled in the art of medicine.

Various modifications and equivalents will be apparent to one skilled in the art and may be made in the compounds, method of treatment, and compositions of the present invention without departing from the spirit or scope thereof, and it is therefore understood that the invention is to be limited only by the scope of the appended claims.

What is claimed is:

1. A compound of the formula:

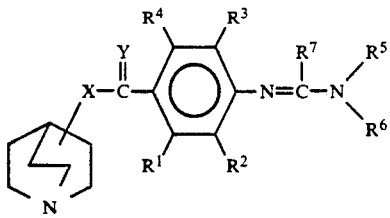

wherein

X=NH attached to 3 or 4 position of 1-azabicyclo[2.2.2]octane;

Y is O or S, $R^1$, $R^2$, $R^3$ and $R^4$ are independently selected from the group consisting of H, halogen, $C_1$-$C_4$ alkyl, $C_1$-$C_4$ alkenyl, $C_1$-$C_4$ alkoxy, and OH;

$R^5$ and $R^6$ are independently selected from the group consisting of H, $C_1$-$C_4$ alkyl and cycloalkyl, or $R^5$ and $R^6$ together with the interposed nitrogen form a 5 or 6 membered heteroalicyclic ring;

$R^7$ is H or methyl, the stereoisomers, the N-oxides and the pharmaceutically acceptable salts thereof.

2. A compound according to claim 1 which is N-(1-azabicyclo[2.2.2]oct-3-yl)-5-chloro-4-[[(dimethylamino)methylene]amino]-2-methoxybenzamide, a stereoisomer or a pharmaceutically acceptable salt thereof.

3. A compound according to claim 1 which is N-(1-azabicyclo[2.2.2]oct-3-yl)-5-chloro-4-[[1-(dimethylamino)ethylene]amino]-2-methoxybenzamide, a stereoisomer or a pharmaceutically acceptable salt thereof.

4. A compound according to claim 1 which is N-(1-azabicyclo[2.2.2]oct-3-yl)-5-chloro-4-[[(1-pyrrolidinyl)methylene]amino]-2-methoxybenzamide, a stereoisomer or a pharmaceutically acceptable salt thereof.

5. A compound according to claim 1 which is N-(1-azabicyclo[2.2.2]oct-4-yl)-5-chloro-4-[[(dimethylamino)methylene]amino]-2-methoxybenzamide, a stereoisomer or a pharmaceutically acceptable salt thereof.

6. A compound according to claim 1 which is N-(1-azabicyclo[2.2.2]oct-3-yl)-5-chloro-4-[[(dimethylamino)methylene]amino]-2-hydroxybenzamide, a stereoisomer or a pharmaceutically acceptable salt thereof.

7. A method of treatment for increasing gastric emptying in warm blooded animals which comprises internal administration of a therapeutically effective amount of a compound of the formula:

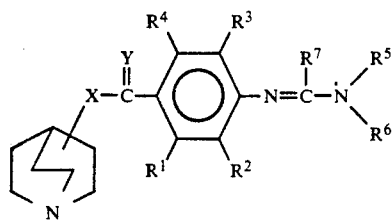

wherein

X=NH attached to 3 or 4 position of 1-azabicyclo[2.2.2] octane;

Y is O or S, $R^1$, $R^2$, $R^3$ and $R^4$ are independently selected from the group consisting of H, halogen, $C_1$-$C_4$ alkyl, $C_1$-$C_4$ alkenyl, $C_1$-$C_4$ alkoxy, and OH;

$R^5$ and $R^6$ are independently selected from the group consisting of H, $C_1$-$C_4$ alkyl and cycloalkyl, or $R^5$ and $R^6$ together with the interposed nitrogen form a 5 or 6 membered heteroalicyclic ring;

$R^7$ is H or methyl, the stereoisomers, the N-oxides and the pharmaceutically acceptable salts thereof.

8. A method of treatment for emesis in warm blooded animals which comprises internal administration of a therapeutically effective amount of a compound of the formula:

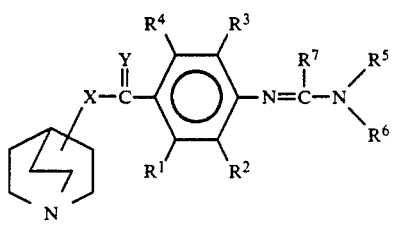

wherein

X=NH attached to 3 or 4 position of 1-azabicyclo[2.2.2] octane;

Y is O or S, $R^1$, $R^2$, $R^3$ and $R^4$ are independently selected from the group consisting of H, halogen, $C_1$-$C_4$ alkyl, $C_1$-$C_4$ alkenyl, $C_1$-$C_4$ alkoxy, and OH;

$R^5$ and $R^6$ are independently selected from the group consisting of H, $C_1$-$C_4$ alkyl and cycloalkyl, or $R^5$ and $R^6$ together with the interposed nitrogen form a 5 or 6 membered heteroalicyclic ring;

$R^7$ is H or methyl, the stereoisomers, the N-oxides and the pharmaceutically acceptable salts thereof.

9. A method of treating anxiety in warm blooded animals which comprises internal administration of a therapeutically effective amount of a compound of the formula:

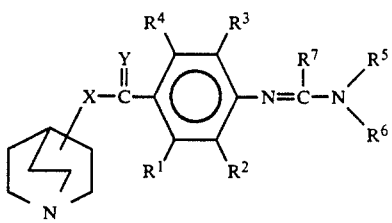

wherein

X=NH attached to 3 or 4 position of 1-azabicyclo[2.2.2] octane;

Y is O or S, $R^1$, $R^2$, $R^3$ and $R^4$ are independently selected from the group consisting of H, halogen, $C_1$-$C_4$ alkyl, $C_1$-$C_4$ alkenyl, $C_1$-$C_4$ alkoxy, and OH;

$R^5$ and $R^6$ are independently selected from the group consisting of H, $C_1$-$C_4$ alkyl and cycloalkyl, or $R^5$ and $R^6$ together with the interposed nitrogen form a 5 or 6 membered heteroalicyclic ring;

$R^7$ is H or methyl, the stereoisomers, the N-oxides and the pharmaceutically acceptable salts thereof.

10. A pharmaceutical composition for treating emesis and anxiety and for increasing gastric emptying comprising:

a. a therapeutically effective amount of a compound of the formula:

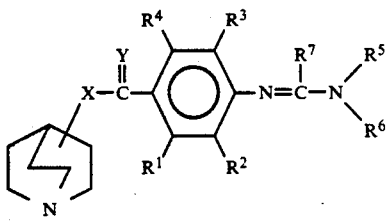

wherein

X=NH attached to 3 or 4 position of 1-azabicyclo[2.2.2] octane;

Y is O or S, $R^1$, $R^2$, $R^3$ and $R^4$ are independently selected from the group consisting of H, halogen, $C_1$-$C_4$ alkyl, $C_1$-$C_4$ alkenyl, $C_1$-$C_4$ alkoxy, and OH;

$R^5$ and $R^6$ are independently selected from the group consisting of H, $C_1$-$C_4$ alkyl and cycloalkyl, or $R^5$ and $R^6$ together with the interposed nitrogen form a 5 or 6 membered heteroalicyclic ring;

$R^7$ is H or methyl, the stereoisomers, the N-oxides and the pharmaceutically acceptable salts thereof, and b. A pharmaceutically acceptable carrier thereof.

* * * * *